(12) United States Patent
Zhu et al.

(10) Patent No.: US 11,540,739 B2
(45) Date of Patent: Jan. 3, 2023

(54) SKIN SODIUM MEASUREMENT USING BIOIMPEDANCE

(71) Applicant: Fresenius Medical Care Holdings, Inc., Waltham, MA (US)

(72) Inventors: Fansan Zhu, Flushing, NY (US); Peter Kotanko, New York, NY (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

(21) Appl. No.: 17/720,521

(22) Filed: Apr. 14, 2022

(65) Prior Publication Data

US 2022/0240806 A1 Aug. 4, 2022

Related U.S. Application Data

(62) Division of application No. 16/712,029, filed on Dec. 12, 2019, now Pat. No. 11,330,998.

(60) Provisional application No. 62/783,581, filed on Dec. 21, 2018.

(51) Int. Cl.
| | |
|---|---|
| A61B 5/0537 | (2021.01) |
| A61B 5/0531 | (2021.01) |
| A61B 5/055 | (2006.01) |
| A61B 5/145 | (2006.01) |
| A61B 5/1477 | (2006.01) |
| A61B 5/00 | (2006.01) |

(52) U.S. Cl.
CPC .......... *A61B 5/0537* (2013.01); *A61B 5/055* (2013.01); *A61B 5/0531* (2013.01); *A61B 5/1477* (2013.01); *A61B 5/14546* (2013.01); *A61B 5/443* (2013.01); *A61B 5/7225* (2013.01); *A61B 5/7246* (2013.01); *A61B 5/7275* (2013.01); *A61B 5/7278* (2013.01); *A61B 5/0004* (2013.01)

(58) Field of Classification Search
CPC ..... A61B 5/0537; A61B 5/0531; A61B 5/055; A61B 5/14546; A61B 5/1477; A61B 5/443; A61B 5/7225; A61B 5/7246; A61B 5/7275; A61B 5/7278; A61B 5/0004; A61B 5/4869
See application file for complete search history.

(56) References Cited

U.S. PATENT DOCUMENTS

| | | |
|---|---|---|
| 4,291,708 A | 9/1981 | Frei et al. |
| 2004/0242976 A1 | 12/2004 | Abreu |
| 2006/0085049 A1 | 4/2006 | Cory et al. |
| 2006/0100532 A1 | 5/2006 | Bae et al. |

(Continued)

FOREIGN PATENT DOCUMENTS

EP 1455646 B1 6/2007

OTHER PUBLICATIONS

U.S. Appl. No. 16/712,029, filed Dec. 12, 2019, Peter Kotanko.

(Continued)

*Primary Examiner* — Devin B Henson
*Assistant Examiner* — Justin Xu
(74) *Attorney, Agent, or Firm* — Bass Patent Law, LLC

(57) ABSTRACT

A technique for determining skin sodium content using bioimpedance spectroscopy includes applying a current at a predetermined frequency to skin of a subject, measuring a voltage across the skin of the subject produced by the current, determining a resistance across the skin of the (Continued)

subject at the predetermined frequency using the measured voltage, and determining skin sodium content using the measured voltage.

20 Claims, 5 Drawing Sheets

(56) References Cited

U.S. PATENT DOCUMENTS

2013/0053673 A1 2/2013 Brunswick
2014/0221792 A1 8/2014 Miller et al.

OTHER PUBLICATIONS

Birgersson et al. "A Methodology for Extracting the Electrical Properties of Human Skin" Physiological Measurement, 2013, pp. 723-736.
ISA, PCT Application No. PCT/US19/65949 International Search Report and Written Opinion dated Feb. 14, 2020. 17 Pages.
Lackermeier, et al., "In Vivo AC Impedance Spectroscopy of Human Skin," Analysis New York Academy of Sciences, vol. 873, pp. 197-219 (1999).
Linz, Peter, et al. "Skin sodium measured with 23Na MRI at 7.0 T," NMR Biomed 2015, pp. 28: 54-62.
Birgersson, Ulrik, "Electrical Impedance of Human Skin and Tissue Alterations: Mathematical Modeling and Measurements," Department of Clinical Science, Intervention and Technology, Karolinska Institute, Stockholm Sweden (2011), 67 pages.
Oltulu, P. et al. "Measurement of Epidermis, Dermis, and Total Skin Thicknesses from Six Different Body Regions with a New Ethical Histometric Technique," Turkish Journal of Plastic Surgery, pp. 26:56-61, 2018.
Rigaud, Bernard, et al., "Bioelectrical Impedance Techniques in Medicine," Critical Reviews in Biomedical Engineering, 24(4-6), Jan. 1, 1996, pp. 257-351.
Schwan, Herman P., Advances in Biological and Medical Physics, pp. 147-224 (John H. Lawrence & Cornelius A. Tobias, eds., vol. 5, Jan. 1957), ISBN: 978-1-4832-3111-2.
University of Oslo, "What is Bioimpedance?" 2011, University of Oslo Department of Physics, 2011, 4 pages.
U.S. Appl. No. 16/712,029, filed Mar. 3, 2022, Notice of Allowance, 9 pages.
U.S. Appl. No. 16/712,029 Non-Final Office Action dated Oct. 22, 2021, 18 pages.
WIPO PCT Application No. PCT/US19/65949, International Preliminary Report on Patentability dated Jul. 1, 2021, 13 pages.
Zhu, Fansan, et al. "Body Composition Modeling in the Calf using an Equivalent Circuit Model of Multi-Frequency Bioimpedance Analysis," Physiol. Meas. 26, pp. S133-S143 (2005).

SKIN SODIUM MEASUREMENT USING BIOIMPEDANCE

CROSS-REFERENCE TO RELATED APPLICATIONS

This application is a divisional of U.S. patent application Ser. No. 16/712,029 filed on Dec. 12, 2019, which claims priority to U.S. Provisional Patent Application No. 62/783,581 filed on Dec. 21, 2018, where the entire contents of each of the foregoing are hereby incorporated by reference herein.

FIELD

The present disclosure generally relates to skin sodium detection and measurement, and, in particular, the present disclosure relates to devices, systems, and methods for the detection and measurement of skin sodium using bioimpedance spectroscopy.

BACKGROUND

Research has shown that the sodium (Na+) content of skin, rather than serum sodium, is associated with systolic blood pressure and left ventricular mass (LVM) in chronic kidney disease (CKD) patients. LVM may thus be an important indicator for use in predicting CKD patient outcomes. Moreover, skin sodium content may be a predictor of outcomes or health attributes in non-CKD patients, such as hypertensive and diabetic patients, among others.

Typically, measurement of skin sodium is performed by sodium-magnetic resonance imaging (i.e., $^{23}$Na-MRI). And, for example, it has been shown that skin sodium measured with sodium-magnetic resonance imaging differed significantly between healthy and hypertensive subjects. While relatively well-established, sodium-magnetic resonance imaging can suffer from several shortcoming, such as: (i) patients having medical contraindications to an MRI, (ii) being performed only on specific and limited region(s) of a patient (e.g., the calf), (c) having limited availability, (d) and having excessive costs. For example, because of the relative limited availability, a patient may have to travel to a properly equipped medical center for sodium-magnetic resonance imaging, and few such medical centers may exist, which can present a logistical challenge for patients.

There thus remains a need for improved skin sodium detection and measurement techniques, e.g., that can overcome some of the challenges of sodium-magnetic resonance imaging.

SUMMARY

In an aspect, a method for determining skin sodium content using bioimpedance spectroscopy includes applying a current at a predetermined frequency to skin of a subject, measuring a voltage across the skin of the subject produced by the current, determining a resistance across the skin of the subject at the predetermined frequency using the measured voltage, and determining skin sodium content using the measured voltage.

Implementations may include one or more of the following features. The method may further include calculating skin resistivity at the predetermined frequency, where the skin sodium content is determined at least in part using the calculated skin resistivity. The skin resistivity ($\rho_{SR}$) may be calculated using a formula, $R_F*A/L$, where $R_F$ is the resistance at the predetermined frequency, A is a cross-sectional area of a measurement region of the skin, and L is a distance between electrodes that measured the voltage. The predetermined frequency may be in a range between 1 Hertz (Hz) and 1 megahertz (MHz). The predetermined frequency may be 1 kHz or less. Skin sodium content (SSC) may be determined using a regression model. The regression model may include a formula, $SSC=a*\rho_{SR}+b*age+c$, where $\rho_{SR}$ is calculated skin resistivity, and where a, b, and c are constant coefficients configured to correlate skin sodium content obtained by sodium-magnetic resonance imaging with skin resistivity obtained by bioimpedance spectroscopy. The current may be applied to dermis of the subject. The predetermined frequency may be selected to traverse through dermis of the subject. The method may further include altering the predetermined frequency, and repeating measurement of the voltage and determining the resistance at the altered frequency to determine a tissue type of the subject. The method may further include selecting the altered frequency determined to provide skin resistivity for dermis of the subject. The method may further include determining one or more of a conductivity and a dielectric constant for current applied at a plurality of different frequencies. The method may further include determining a slope for one or more of the conductivity and the dielectric constant between at least two of the plurality of different frequencies. The method may further include determining a tissue type using the slope. The tissue type may include one of skin, fat, and muscle. The tissue types of fat and muscle may be disregarded for calculating skin sodium content. The tissue type may include one of epidermis, dermis, and subcutaneous layer. All tissue types except the dermis may be disregarded for calculating skin sodium content. The slope may be defined as a difference in conductivity, $\Delta\sigma$, between the at least two of the plurality of different frequencies divided by a step frequency ($\Delta\sigma/1$ Hz). The method may further include associating the skin sodium content with a physiological characteristic to determine a predictive health condition of the subject. The physiological characteristic may include one or more of systolic blood pressure, left ventricular mass, and a hydration status. The predictive health condition may include one or more of chronic kidney disease, hypertension, and diabetes. The method may further include transmitting data to a computing device, the data including one or more of the predetermined frequency, the voltage, the resistance, skin resistivity, and the skin sodium content. The method may further include measuring extracellular volume (ECV) and intracellular volume (ICV) of the skin. The method may further include continuously calculating skin sodium content for a predetermined time period. The method may further include transmitting a notification when skin sodium content is outside of a predetermined range.

In an aspect, an apparatus for measuring skin sodium content using bioimpedance spectroscopy includes a current generator structurally configured to produce a current at a predetermined frequency to apply to skin of a subject, a controller operable to adjust the predetermined frequency, a sensor structurally configured to measure voltage across the skin of the subject produced by the current, and at least one processor configured to determine skin sodium content using the measured voltage.

Implementations may include one or more of the following features. The processor may be configured to compute bioimpedance based on the measured voltage and to determine skin sodium content using the computed bioimpedance. One or more of the current generator and the sensor may include a plurality of electrodes. The controller may be operable to control the current generator to produce current at a plurality of different frequencies. The processor may be configured to determine one or more of a conductivity and a dielectric constant for current applied at the plurality of different frequencies. The processor may be configured to determine a slope for one or more of the conductivity and the dielectric constant between at least two of the plurality of different frequencies. The processor may be configured to determine a tissue type using the slope. The apparatus may further include a computing device in communication with the at least one processor.

These and other features, aspects, and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

Figure 1:
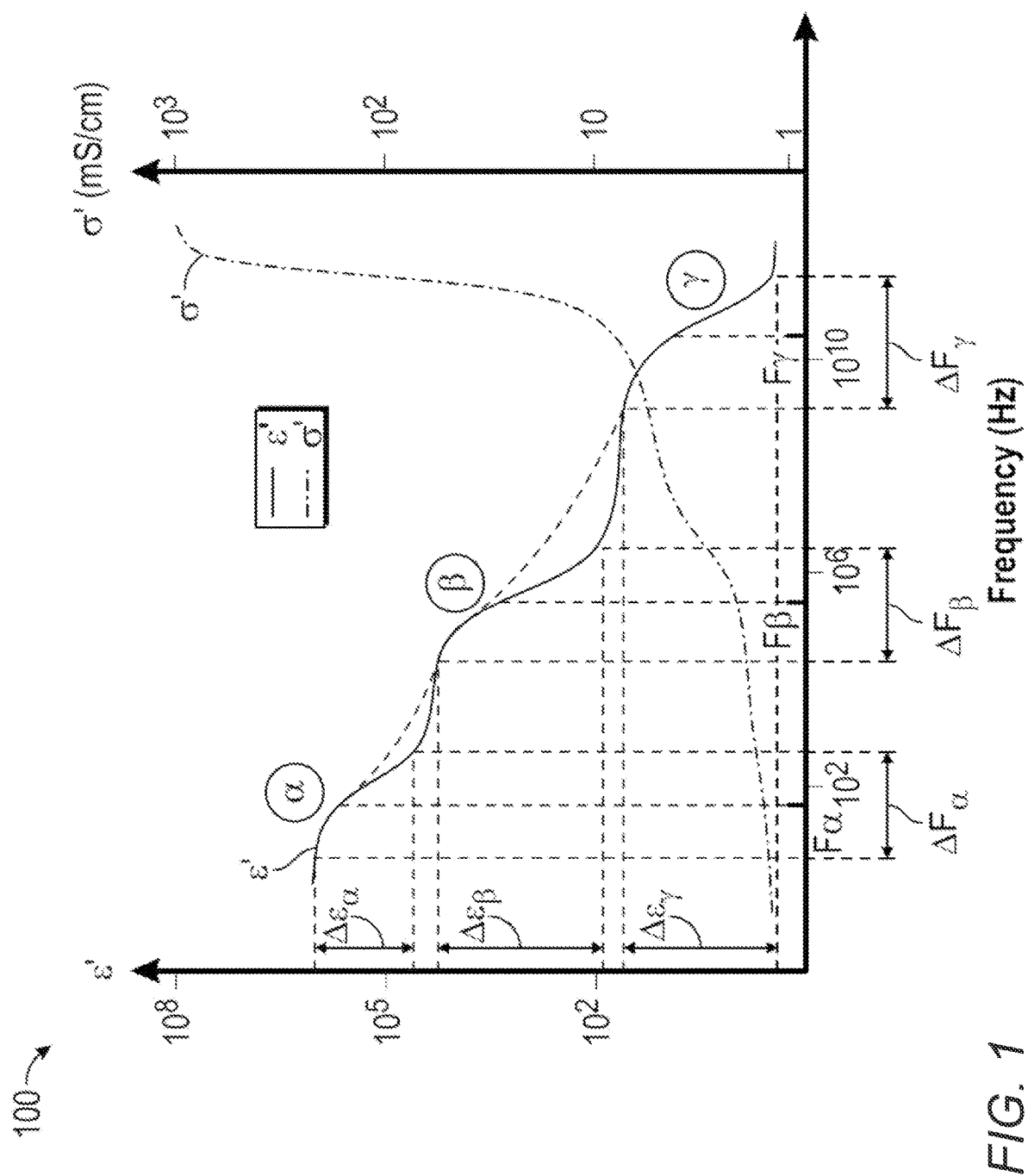
FIG. 1 is a graph showing the relationship between frequency and muscle electrical properties (dielectric constant ε and conductivity σ), in accordance with a representative embodiment.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods disclosed herein generally relate to skin sodium detection and measurement using bioimpedance spectroscopy. More particularly, the devices, systems, and methods disclosed herein may be used for the determination and quantification of sodium storage (e.g., osmotic inactive sodium storage) in glycosaminoglycan molecules in the skin. As discussed above, skin sodium content may be useful for determining or predicting physiological conditions or characteristics of a patient, e.g., systolic blood pressure and left ventricular mass (LVM) in chronic kidney disease (CKD) patients, and for predicting outcomes in non-CKD patients, such as hypertensive and diabetic patients, among others. As further discussed above, typically skin sodium content is obtained through sodium-magnetic resonance imaging (i.e., $^{23}$Na-MRI), which has various pitfalls. The present teachings, however, generally set forth devices, systems, and methods for skin sodium measurement using bioimpedance spectroscopy, which may overcome some of the pitfalls of skin sodium measurement using sodium-magnetic resonance imaging.

Bioimpedance spectroscopy has been used to distinguish body fluid compartments using multi-frequency current—e.g., using about 1 kilohertz (kHz) to about 1 megahertz (MHz) current. For example, extracellular volume (ECV) and intracellular volume (ICV) compartments can be measured using bioimpedance spectroscopy. This is based on the general principle that alternating current (AC) with a frequency less than about 10 kHz can only pass through ECV, while AC with a frequency greater than about 300 kHz can pass through both ECV and ICV.

FIG. 1 is a graph showing the relationship between frequency and muscle electrical properties (dielectric constant c and conductivity σ), in accordance with a representative embodiment. Specifically, the graph 100 shows that the dielectric constant (ε) and conductivity (σ) of muscle changes with the increase in AC frequency (see also Herman P. Schwan, ADVANCES IN BIOLOGICAL AND MEDICAL PHYSICS, pp.

147-224 (John H. Lawrence & Cornelius A. Tobias eds., Vol. 5, January 1957), ISBN: 978-1-4832-3111-2, which is hereby incorporated by reference in its entirety).

FIG. 1 indicates three dispersions ($\alpha$, $\beta$, $\gamma$) in the dielectric constant ($\varepsilon$) when the frequency of current is increased, where the mechanisms of these dispersions have been explained in Schwan, which is cited above and incorporated by reference. However, this study was limited to muscle and thus may not necessarily correlate to the electrical properties of the skin or other tissue. Thus, in general, to detect skin electrical properties, the present teachings may include using an AC frequency of less than about 1 kHz. For example, by using a range of AC frequencies of about 0.01-1.00 kHz, the relationship between different skin layers and AC frequencies can be obtained.

While skin bioimpedance has been used for evaluating skin conditions, such as skin thickness (see, e.g., Ulrik Birgersson, "Electrical Impedance of Human Skin and Tissue Alterations: Mathematical Modeling and Measurements," Department of Clinical Science, Intervention and Technology, Karolinska Institutet, Stockholm, Sweden (2011), which is incorporated by reference herein), the relationship between skin sodium concentration and body conductivity has generally not been investigated. Using the present teachings, however, bioimpedance spectroscopy may be used to measure skin sodium content, e.g., for replacing or supplementing sodium-magnetic resonance imaging.

Figure 2:
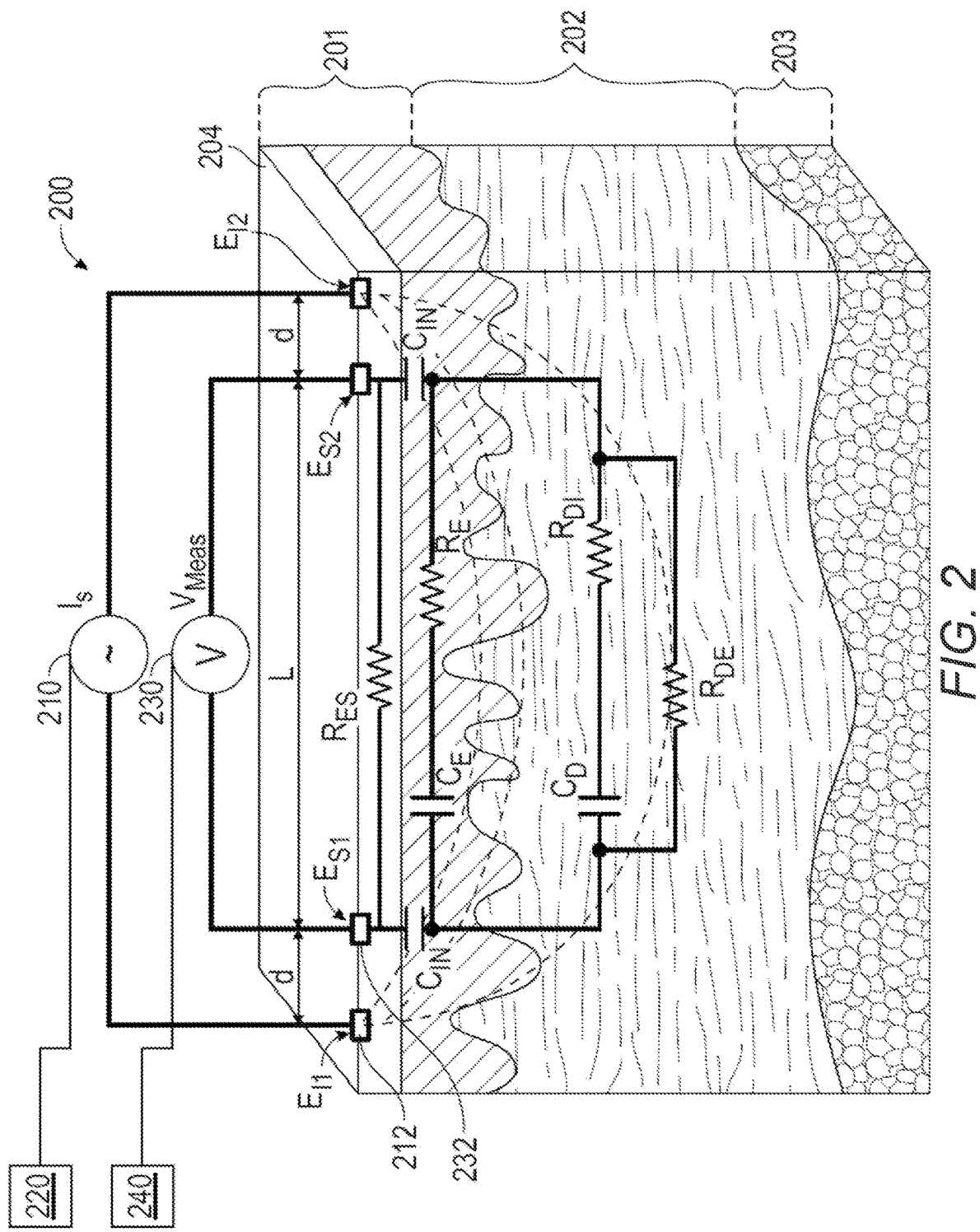
FIG. 2 illustrates an electrical model of an apparatus for measuring skin sodium content using bioimpedance spectroscopy, in accordance with a representative embodiment.

FIG. 2 illustrates an electrical model of an apparatus for measuring skin sodium content using bioimpedance spectroscopy, in accordance with a representative embodiment. In general, and as shown in the figure, the apparatus 200 may include a current generator 210, a controller 220, a sensor 230, and a processor 240.

In particular, FIG. 2 shows a skin electrical model with bioimpedance measurement to describe the composition of skin—where each of the epidermis 201, the dermis 202, and the subcutaneous layer 203 are shown. In the figure, $I_S$ represents current (e.g., a multifrequency AC) that is produced by the current generator 210, controlled by the controller 220, and injected into the skin surface 204 by injecting electrodes 212 (also represented by $E_{I1}$ and $E_{I2}$ in the figure) or the like. Also, in the figure, $V_{Meas}$ represents a voltage measured by the sensor 230, which may include sensing electrodes 232 (e.g., two sensing electrodes 232 also represented by $E_{S1}$ and $E_{S2}$ in the figure). Continuing on with the electrical model representation of the apparatus 200 in the figure: $R_{ES}$ represents the resistance of the epidermis 201; $C_E$ and $R_E$ represent the capacitance and resistance of the inner portion of the epidermis 201, respectively; $C_{IN}$ represents the capacitance between the skin surface 204 and the inner portion of the epidermis 201; $R_{DI}$ and $R_{DE}$ represent the resistance of the intracellular and extracellular dermis 202; CD represents capacitance of the dermis 202; L is the distance between the sensing electrodes 232; and d is the distance between the sensing electrodes 232 and the injecting electrodes 212. It will be understood that, generally, L and d can be nearly any distances.

The current generator 210 may be structurally configured to produce a current ($I_S$) at a predetermined frequency to apply to the skin of a subject, such as a medical patient (e.g., a CKD patient or a non-CKD patient). As discussed above, the current generator 210 may include, or may otherwise be coupled in electrical communication with a plurality of electrodes, e.g., at least two injecting electrodes 212 as shown in the figure. The electrodes may include any as known in the art, such as surface-type conductive pads that include an electrically conductive electrolyte gel (e.g., potassium chloride or silver chloride) and a metal conductor (e.g., a silver/silver chloride conductor)—e.g., standard ECG electrodes or the like. Thus, one or more of the injecting electrodes 212 and the sensing electrodes 232 may include adhesive-type electrodes that adhere to, or are otherwise coupled with, a surface of a patient's skin. One or more of the injecting electrodes 212 and the sensing electrodes 232 may also or instead include penetrating electrodes (e.g., needle-type electrodes). In some implementations, a combination of adhesive-type electrodes and needle-type electrodes may be used. Other electrodes are also or instead possible for one or more of the injecting electrodes 212 and the sensing electrodes 232.

It will be further understood that the number of electrodes may vary in the apparatus 200, a system including the apparatus 200, or in use of the techniques otherwise described herein. For example, although FIG. 2 shows two injecting electrodes 212 and two sensing electrodes 232, more or less electrodes are possible. By way of example, an implementation may include three or more (e.g., four) injecting electrodes 212.

The skin surface 204 may include one or more of fractal, micro-porous, and nano-porous surface characteristics. In the apparatus 200, one or more of the electrodes may be specifically tailored to be used with a particular skin surface 204.

As discussed above, the current generator 210 may be structurally configured to produce a current ($I_S$) at a predetermined frequency to apply to the skin of a subject. It will be understood that the predetermined frequency discussed herein may include a frequency range rather than an exact frequency, unless explicitly stated to the contrary or otherwise clear from the context. For example, the predetermined frequency may be between about 1 Hz and about 1 MHz, e.g., about 1 kHz or less. This may be significantly less than frequencies that are typically used in bioimpedance spectroscopy, namely because bioimpedance spectroscopy of the skin is not desired in typical use cases apart from the present teachings. Other frequencies are also or instead possible, e.g., frequencies as low as 0.1 Hz.

The controller 220 may be operable to adjust the predetermined frequency that is produced by the current generator 210. Specifically, the controller 220 may be operable to control the current generator 210 to produce current at a plurality of different frequencies, which can be useful in determining the tissue type through which the current is passing, and thus the tissue type where a measurement is derived. That is, and as further explained throughout this disclosure, different frequencies may penetrate and travel through different regions of tissue of a subject, and, when a measurement of a voltage or resistance is desired at a specific tissue region (e.g., at the dermis 202 to find the skin resistivity and the skin sodium content of the dermis 202), a specific, predetermined current may be used that penetrates and travels through the specific tissue region. However, the predetermined current that penetrates and travels through a specific tissue region for one subject may be different than the predetermined current that penetrates and travels through the same tissue region in a different subject. Further, even the same subject can have fluctuations in their condition or state that cause a change in frequency penetration aspects for that subject, e.g., on a day-to-day basis or otherwise. Therefore, a technique may be used to find a specific frequency associated with a specific tissue region in a specific patient at a specific time.

By way of example, a current that penetrates and travels through the epidermis 201 may be between about 0 Hz and about 10 Hz (see Lackermeier, et al., "In Vivo AC Impedance Spectroscopy of Human Skin," Analysis New York Academy of Sciences Vol. 873, pp. 197-213 (1999), which is hereby incorporated by reference in its entirety), a current that penetrates and travels through the dermis 202 may be between about 10 Hz and about 1 kHz, a current that penetrates and travels through adipose tissue may be between about 100 Hz and about 10 kHz, a current that penetrates and travels through ECV may be between about 1 kHz and about 50 kHz, and a current that penetrates and travels through ICV may be between about 20 kHz and about 1 MHz. Other current values are also or instead possible.

The sensor 230 may be structurally configured to measure voltage ($V_{Meas}$) across the skin of the subject, where the voltage is produced by the current ($I_S$) applied by the current generator 210. As discussed above, the sensor 230 may include, or may otherwise be in communication with, a plurality of electrodes, e.g., at least two sensing electrodes 232 as shown in the figure. The electrodes may include any as described herein or as commonly known in the art for measuring voltage across a substrate such as the skin of a subject.

The processor 240 may be configured to determine skin sodium content using the measured voltage ($V_{Meas}$). Specifically, the processor may be configured to compute bioimpedance based on the measured voltage, and to determine skin sodium content using the computed bioimpedance.

The processor 240 may also or instead be configured to determine one or more of a conductivity and a dielectric constant for current applied at a plurality of different frequencies. Further, the processor 240 may be configured to determine a slope for one or more of the conductivity and the dielectric constant between at least two of the plurality of different frequencies. In this manner, as described herein, the processor 240 may be configured to determine a tissue type using the slope. This may be useful for determining the predetermined frequency to obtain a voltage measurement (and thus a resistance) at the dermis 202, which may be of interest for obtaining skin sodium content of the skin of the subject.

Figure 3:
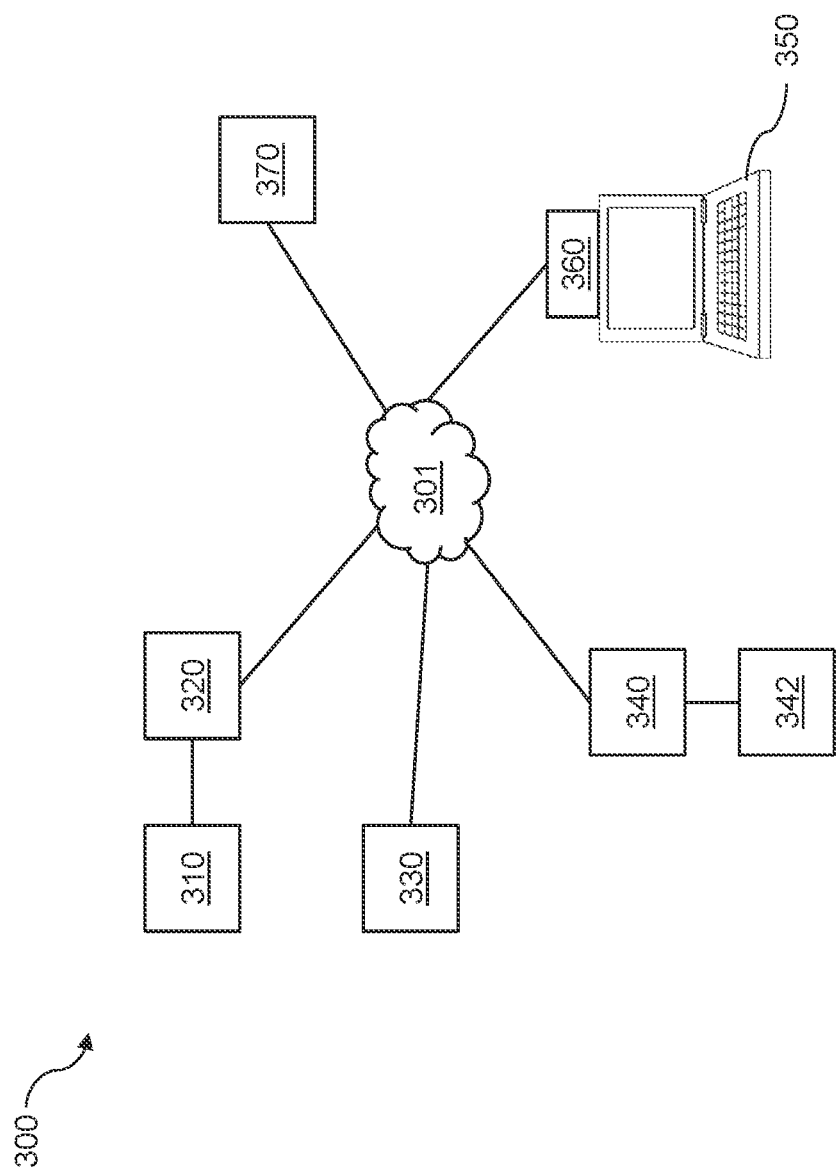
FIG. 3 illustrates a system for measuring skin sodium content using bioimpedance spectroscopy, in accordance with a representative embodiment.

FIG. 3 illustrates a system for measuring skin sodium content using bioimpedance spectroscopy, in accordance with a representative embodiment. The system 300 may generally include one or more components of an apparatus for measuring skin sodium content using bioimpedance spectroscopy such the apparatus described above with reference to FIG. 2, along with other components in communication with one another over a data network 301 or the like. For example, the system 300 may include a current generator 310, a controller 320, a sensor 330, a processor 340, a memory 342, a computing device 350, a communications interface 360, and other resources 370 (e.g., other hardware or external resources), where one or more of the components of the system 300 are in communication or are otherwise connected over the data network 301.

The current generator 310, controller 320, sensor 330, and processor 340 may be the same or similar to those described above. Additionally, or alternatively, the controller 320 may include, or otherwise be in communication with, the processor 340, the memory 342, a user device such as the computing device 350, and so on, for controlling one or more of the components of the system 300. Thus, in general, the controller 320 may be electronically coupled (e.g., wired or wirelessly) in a communicating relationship with one or more of the components of an apparatus for measuring skin sodium content using bioimpedance spectroscopy.

The controller 320 may be configured to adjust the frequency of the current produced by the current generator 310, e.g., based on signals received from the sensor 330, or instructions received from a user, the processor 340, or otherwise. In general, the controller 320 may be electrically coupled in a communicating relationship, e.g., an electronic communication, with any of the components of the system 300. In general, the controller 320 may be operable to control the components of the system 300, and may include any combination of software and/or processing circuitry suitable for controlling the various components of the system 300 described herein including without limitation processors, microprocessors, microcontrollers, application-specific integrated circuits, programmable gate arrays, and any other digital and/or analog components, as well as combinations of the foregoing, along with inputs and outputs for transceiving control signals, power signals, sensor signals, and the like. In certain implementations, the controller 320 may include the processor 340 or other processing circuitry with sufficient computational power to provide related functions such as executing an operating system, providing a graphical user interface, set and provide rules and instructions for operation of a component of the system 300, convert sensed information into instructions, notifications, and the like, and operate a web server or otherwise host remote operators and/or activity through one or more communications interfaces 360 described below. In certain implementations, the controller 320 may include a printed circuit board, an Arduino controller or similar, a Raspberry Pi controller or the like, a prototyping board, or other computer related components.

The controller 320 may be a local controller disposed on an apparatus for measuring skin sodium content using bioimpedance spectroscopy or another component of the system 300, or a remote device otherwise in communication with the system 300 and its components. For example, one or more of the controller 320 and a user interface in communication with the controller 320 may be disposed on an external component (e.g., a computing device 350 such as a smartphone) in communication with the system 300 over a data network 301.

The processor 340 may include an onboard processor for the apparatus for measuring skin sodium content using bioimpedance spectroscopy or another component of the system 300. The processor 340 may also or instead be disposed on a separate computing device 350 that is connected to the system 300 or one or more of its components through a data network 301, e.g., using the communications interface 360, which may include a Wi-Fi transmitter and receiver. The processor 340 may perform calculations, e.g., calculations to determine resistance across the skin of the subject at a predetermined frequency using a measured voltage, calculations to determine skin resistivity, calculations to determine skin sodium content, and so on.

The processor 340 may be any as described herein or otherwise known in the art. The processor 340 may be included on the controller 320, or it may be separate from the controller 320, e.g., it may be included on a computing device 350 in communication with the controller 320 or another component of the system 300. In an implementation, the processor 340 is included on, or is in communication with, a server that hosts an application for operating and controlling the system 300.

The memory 342 may be any as described herein or otherwise known in the art. The memory 342 may contain computer code and may store data such as sequences of operation for one or more of the components of the system 300 (e.g., the current generator 310), sequences or content for notifications and alerts, historical data (e.g., previous inputs, measurements, and calculations), and so on. The memory 342 may also or instead contain computer executable code stored thereon that provides instructions for the processor 340 for implementation. The memory 342 may include a non-transitory computer readable medium.

The system 300 may further include a computing device 350 in communication with one or more of the components of the system 300 including without limitation the controller 320 and the apparatus for measuring skin sodium content using bioimpedance spectroscopy. The computing device 350 may include a user interface, e.g., in communication with the controller 320 or another component of the system 300.

The computing device 350 may include any devices within the system 300 operated by operators or otherwise to manage, monitor, communicate with, or otherwise interact with other participants in the system 300. This may include desktop computers, laptop computers, network computers, tablets, smartphones, smart watches, PDAs, or any other device that can participate in the system 300 as contemplated herein. In an implementation, the computing device 350 is integral with another participant in the system 300.

The computing device 350 may generally provide a user interface, which may include a graphical user interface, a text or command line interface, a voice-controlled interface, and/or a gesture-based interface. In general, the user interface may create a suitable display on the computing device 350 for operator interaction. In implementations, the user interface may control operation of one or more of the components of the system 300, as well as provide access to and communication with the controller 320, processor 340, and other resources 370. The user interface may be maintained by a locally executing application on the computing device 350 that receives data from one or more of the components of the system 300. In other embodiments, the user interface may be remotely served and presented on a computing device 350, such as where the controller 320 includes a web server that provides information through one or more web pages or the like that can be displayed within a web browser or similar client executing on the computing device 350. In implementations, the user interface may also or instead be provided by and/or disposed on another participant in the system 300.

The data network 301 may be any network(s) or internetwork(s) suitable for communicating data and control information among participants in the system 300. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMAX-Advanced (IEEE 802.16m) and/or other technologies, as well as any of a variety of corporate area or local area networks and other switches, routers, hubs, gateways, and the like that might be used to carry data among participants in the system 300. The data network 301 may include wired or wireless networks, or any combination thereof. One skilled in the art will also recognize that the participants shown the system 300 need not be connected by a data network 301, and thus can be configured to work in conjunction with other participants independent of the data network 301.

Communication over the data network 301, or other communication between components of the devices or systems described herein, may be provided via one or more communications interfaces 360. The communications interface 360 may include, e.g., a Wi-Fi receiver and transmitter to allow the logic calculations to be performed on a separate computing device 350. This may include connections to smartphone applications and the like. More generally, the communications interface 360 may be suited such that any of the components of the system 300 can communicate with one another. Thus, the communications interface 360 may be present on one or more of the components of the system 300. The communications interface 360 may include, or be connected in a communicating relationship with, a network interface or the like. The communications interface 360 may include any combination of hardware and software suitable for coupling the components of the system 300 to a remote device (e.g., a computing device 350 such as a remote computer or the like) in a communicating relationship through a data network 301. By way of example and not limitation, this may include electronics for a wired or wireless Ethernet connection operating according to the IEEE 802.11 standard (or any variation thereof), or any other short or long range wireless networking components or the like. This may include hardware for short range data communications such as Bluetooth or an infrared transceiver, which may be used to couple into a local area network or the like that is in turn coupled to a data network such as the internet. This may also or instead include hardware/software for a WiMAX connection or a cellular network connection (using, e.g., CDMA, GSM, LTE, or any other suitable protocol or combination of protocols). Additionally, the controller 320 may be configured to control participation by the components of the system 300 in any network to which the communications interface 360 is connected, such as by autonomously connecting to the data network 301 to retrieve status updates and the like.

The system 300 may include other resources 370 as described above. In certain implementations, the other resources 370 may include additional sensors, cameras, power sources, gauges, and the like. The other resources 370 may also or instead include input devices such as a keyboard, a touchpad, a computer mouse, a switch, a dial, a button, and the like, as well as output devices such as a display, a speaker or other audio transducer, light emitting diodes or other lighting or display components, and the like. Other resources 370 of the system 300 may also or instead include a variety of cable connections and/or hardware adapters for connecting to, e.g., external computers, external hardware, external instrumentation or data acquisition systems, and the like. The other resources 370 may also or instead include a power source.

The other resources 370 may also or instead include a server, a database or other data storage, a remote resource, a network interface, processing circuitry, and the like. Thus, other resources 370 such as other hardware or other software may be included in addition to, or instead of, components described above.

In an exemplary embodiment of the system 300, the current generator 310 produces current ranging from direct current (DC) to AC from about 1 kHz up to at least about 1 MHz. The controller 320 may be used to adjust the frequency, where the function of the frequency control is to create steps of frequency (Fs) of current that can be associated with a slope of conductivity ($\sigma$), which can then be associated with a tissue region of a subject (it will be understood that the slope of conductivity may be found using a relationship of conductivity to resistivity, i.e., resistivity=1/conductivity). For example, when the slope of conductivity is flattening (e.g., the slope is less than or equal to about 5%), the value may represent the impedance of the epidermis, and as the slope of conductivity reaches a second flattening (e.g., the slope is between about 5-10%), the value may represent the impedance of the dermis. Stated otherwise, skin layers can be distinguished by a change in the slope of conductivity and/or dielectric constant.

The processor 340 or another component of the system 300 may act as an impedance calculator to compute the bioimpedance. Further, the processor 340 or another component of the system 300 may calculate the value of the conductivity at each frequency step. The slope may be defined as the difference in conductivity ($\Delta\sigma$) between the high and low frequency (e.g., between adjacent frequency steps) divided by the step frequency ($\Delta\sigma/1$ Hz). The input data, and functions thereof, as well as the output of results may be transmitted to the computing device 350 such as a smartphone of a user. For example, the output of results may include, but are not limited to, one or more of conductivity and dielectric constant, resistivity, skin sodium content, hydration status, and so on.

Figure 4:
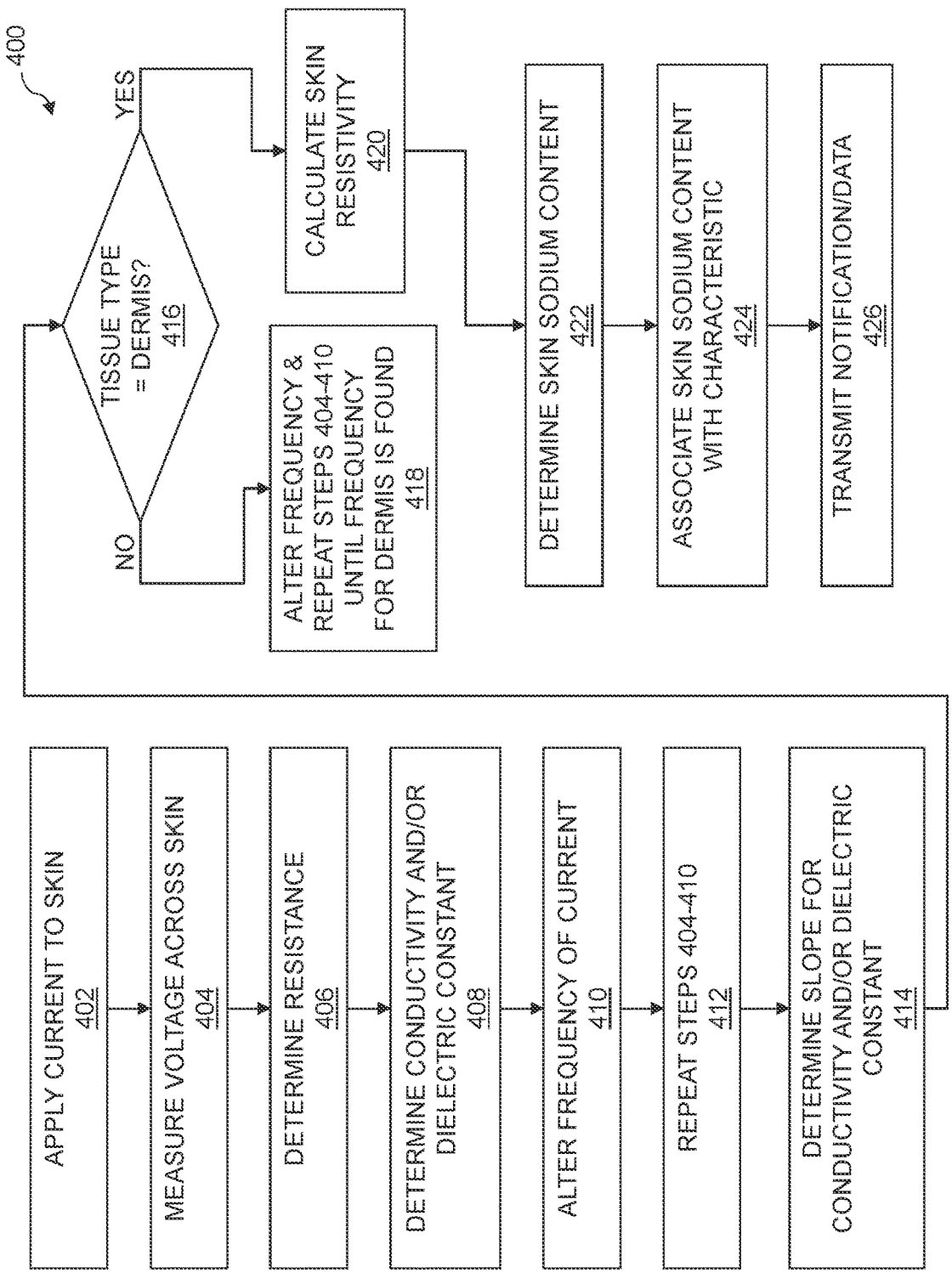
FIG. 4 is a flow chart of a method for determining skin sodium content using bioimpedance spectroscopy, in accordance with a representative embodiment.

FIG. 4 is a flow chart of a method for determining skin sodium content using bioimpedance spectroscopy, in accordance with a representative embodiment. The method 400 may be performed by any of the apparatuses and systems described herein, such as those described with reference to FIGS. 2 and 3 discussed above.

As shown in step 402, the method 400 may include applying a current at a predetermined frequency to the skin of a subject. As discussed herein, a current generator may produce the current, and the current may be injected into the subject's skin via one or more electrodes—e.g., two injecting electrodes.

The predetermined frequency may be a known frequency that will yield a voltage measurement (and thus a resistance) across the dermis, from which a skin sodium content of the dermis can be determined. Thus, the current may be applied directly to the dermis of the subject, without a need for experimentation or discovery, e.g., by simply using the predetermined frequency. However, it will be understood that, in other implementations, the predetermined frequency is one of a plurality of frequencies used to determine a frequency that will yield a voltage measurement (and thus a resistance) across the dermis, from which a skin sodium content of the dermis can be determined. In other words, the predetermined frequency may be selected to traverse through dermis of the subject, e.g., from a plurality of different frequencies that have been applied in a dermis discovery technique. An example of such a dermis discovery technique is further elaborated with reference to steps 408-418 described below.

In general, the predetermined frequency may be a relatively low frequency, particularly in the art of bioimpedance. For example, the predetermined frequency may be between about 1 Hz and about 1 MHz. And, even more specifically, the predetermined frequency may be about 1 kHz or less.

As shown in step 404, the method 400 may include measuring a voltage across the skin of the subject produced by the current. As discussed herein, one or more sensors featuring one or more electrodes may be used to measure the voltage across a subject's skin. In general, the application of the current and the measuring of the voltage can be performed at any location or segment of the body of the subject—e.g., not just the calf, although the calf can certainly be utilized if desired.

As shown in step 406, the method 400 may include determining a resistance across the skin of the subject at the predetermined frequency using the measured voltage. This resistance (or, more generally, the measured voltage) may then be used to calculate skin resistivity (see step 420 below) and to determine skin sodium content (see step 422 below). This resistance (or, more generally, the measured voltage) may also or instead be used as a data point for calculating conductivity and/or a dielectric constant at a particular frequency of current, e.g., for determining a slope between one or more of conductivity or dielectric constants associated with two or more different applied frequencies.

It will be understood that determining a resistance across the skin of the subject at the predetermined frequency using the measured voltage may involve a relatively simple calculation, i.e., using Ohm's Law. It will be further understood that, when the present teachings (i.e., in this method 400, or in any of the devices, systems, apparatuses, and techniques described herein) refer to calculating or computing a characteristic, property, or other data point, this may also or instead include computing any other quantity that is a known, predetermined function thereof. For example, and as explained in the method 400 herein, skin sodium content can be calculated from skin resistivity, which can be calculated from a resistance determined by measuring a voltage across a subject's skin generated from a known, applied current. In this manner, the method 400, and more generally the present teachings, may contemplate and include other techniques for calculating skin sodium content (or other properties) from a measured voltage generated from a known, applied current, or more generally, from properties discoverable by applying a predetermined frequency of current to the subject's skin.

As shown in step 408, the method 400 may include determining one or more of a conductivity and a dielectric constant for current applied at the predetermined frequency (or at a plurality of different frequencies that are applied).

As shown in step 410, the method 400 may include altering the predetermined frequency. This may be done as part of a dermis finding technique, i.e., to determine the frequency to use for determining skin sodium content of the dermis.

As shown in step 412, the method 400 may include repeating one or more of steps 404-410, e.g., repeating measurement of the voltage and determining the resistance at the altered frequency to determine a tissue type of the subject.

As shown in step 414, the method 400 may include determining a slope for one or more of the conductivity and the dielectric constant between at least two of the plurality of different frequencies that are applied to the skin of the subject. The slope may be defined as a difference in conductivity, $\Delta\sigma$, between the at least two different applied frequencies divided by a step frequency ($\Delta\sigma/1$ Hz).

As shown in step 416, the method 400 may include determining a tissue type using the slope, and, when the tissue type is determined to be the dermis, the method 400 may proceed to step 420. Otherwise, the method 400 may proceed to step 418. Stated otherwise, the method 400 may include selecting the altered frequency determined to provide skin resistivity for the dermis of the subject.

Different tissue types that may be determined using this approach may include one or more of skin, fat, and muscle. In this instance, tissue types of fat and muscle may be disregarded for calculating skin sodium content. Also, or instead, different tissue types that may be determined using this approach may include one or more of the epidermis, the dermis, and the subcutaneous layer. In this instance, all tissue types except for the dermis may be disregarded for calculating skin sodium content. Currency density and change in reactance may also or instead be used for determining tissue type.

As shown in step 418, the method 400 may include altering the predetermined frequency and repeating one or more of steps 404-410, e.g., until the frequency that will yield a voltage measurement (and thus a resistance) across the dermis is found, from which a skin sodium content of the dermis can be determined.

As shown in step 420, the method 400 may include calculating skin resistivity at the predetermined frequency— e.g., the frequency known or determined to produce a voltage measurement for the dermis. It will be understood that the skin sodium content may be determined at least in part using a calculated skin resistivity. The skin resistivity ($\rho_{SR}$) may be calculated using the following formula:

$$\rho_{SR} = R_F * A/L \qquad \text{Equation 1}$$

In Equation 1 above, $R_F$ is the resistance at the predetermined frequency, A is a cross-sectional area of a measurement region of the skin, and L is a distance between electrodes (or other sensors) that measured the voltage. It will be understood that the cross-sectional area of a measurement region of the skin, A, may be dependent upon placement of the electrodes and the region of the body of the subject to which the electrodes are applied. The cross-sectional area, A, can be calculated by using the equation $A=C^2/4\pi$, where C is the circumference and L is the length of measurement of the region of the skin (e.g., the calf of a human patient). Using the example implementation of the region of the skin being the calf of a human patient, the circumference, C, may be measured from the surface of the calf. The cross-sectional area, A, of the calf may include skin, fat, muscle, and bone. If the thickness of the skin is known, the cross-sectional area, A, of the skin can be calculated so that resistivity in the skin can then be calculated as described herein. The thickness of skin may vary based on the age, gender, and its location. For example, total thickness of human skin (epidermis and dermis) may be between about 2 mm to about 6 mm (see Oltulu P., et al., "Measurement of Epidermis, Dermis, and Total Skin Thicknesses from Six Different Body Regions with a New Ethical Histometric Technique," Turkish Journal of Plastic Surgery, 26:56-61, 2018—hereby incorporated by reference herein). The exact value of the thickness may also or instead be found according to experimental data.

As shown in step 422, the method 400 may include determining skin sodium content using the measured voltage. The skin sodium content may be calculated according to resistivity, age, and one or more constants. More specifically, the skin sodium content (SSC) may be determined using a regression model. For example, the regression model may include the following formula:

$$SSC = a*\rho_{SR} + b*age + c \qquad \text{Equation 2}$$

In Equation 2 above, $\rho_{SR}$ is the calculated skin resistivity, and 'age' is the age of the subject. Further, in Equation 2 above, a, b, and c are constant coefficients configured to correlate skin sodium content obtained by sodium-magnetic resonance imaging with skin resistivity obtained by bioimpedance spectroscopy. These constants may be obtained from validation studies of the present teachings, e.g., that allow for a correlation of skin sodium content obtained from sodium-magnetic resonance imaging versus bioimpedance spectroscopy.

It will be understood, however, that Equation 2 above is not the only functional relationship between skin sodium content and skin resistivity. For example, other mathematical relationships (e.g., nonlinear, additional coefficients, and independent variable) may also or instead be utilized.

As shown in step 424, the method 400 may include associating the skin sodium content with a physiological characteristic, e.g., to determine a predictive health condition of the subject. By way of example, the physiological characteristic may include one or more of systolic blood pressure and left ventricular mass. Further, by way of example, the physiological characteristic may include a hydration status of the subject. And, by way of further example, the predictive health condition may include one or more of CKD, hypertension, and diabetes.

As shown in step 426, the method 400 may include transmitting a notification (and/or other data), e.g., to a computing device. For example, transmitted data may include one or more of the predetermined frequency, the voltage, the resistance, skin resistivity, and the skin sodium content. By way of further example, the method 400 may include transmitting a notification when skin sodium content is outside of a predetermined range. In this manner, the present teachings may include continuously calculating skin sodium content for a predetermined time period, and transmitting notifications as needed. To this end, the present teachings may include a wearable monitor for skin sodium content.

In some implementations—depending on the size, form, and orientation of the sodium depots—different bio-impedance dispersions may be observed using the present techniques. Thus, the present teachings (e.g., the above method 400) may include determining one or more of the aggregation, form, and orientation of glycosaminoglycan bound sodium depots in the skin.

It will be further understood that, using the techniques discussed herein, the method 400 may further include measuring extracellular volume (ECV) and intracellular volume (ICV) of the skin. Also, or instead, techniques discussed herein may be adapted for use in detecting and measuring other chemical content in a subject or patient—i.e., in addition to, or instead of, skin sodium content—such as potassium and the like. That is, other bioelectric materials and the like could be detected and measured using an adaptation of the present teachings. For example, ionic compositions may be detected and measured at higher frequencies than that used for sodium. Also, or instead, intracellular chemicals may be detected and measured using the present teachings, although discovering the frequencies for such intracellular chemicals may be challenging.

Figure 5:
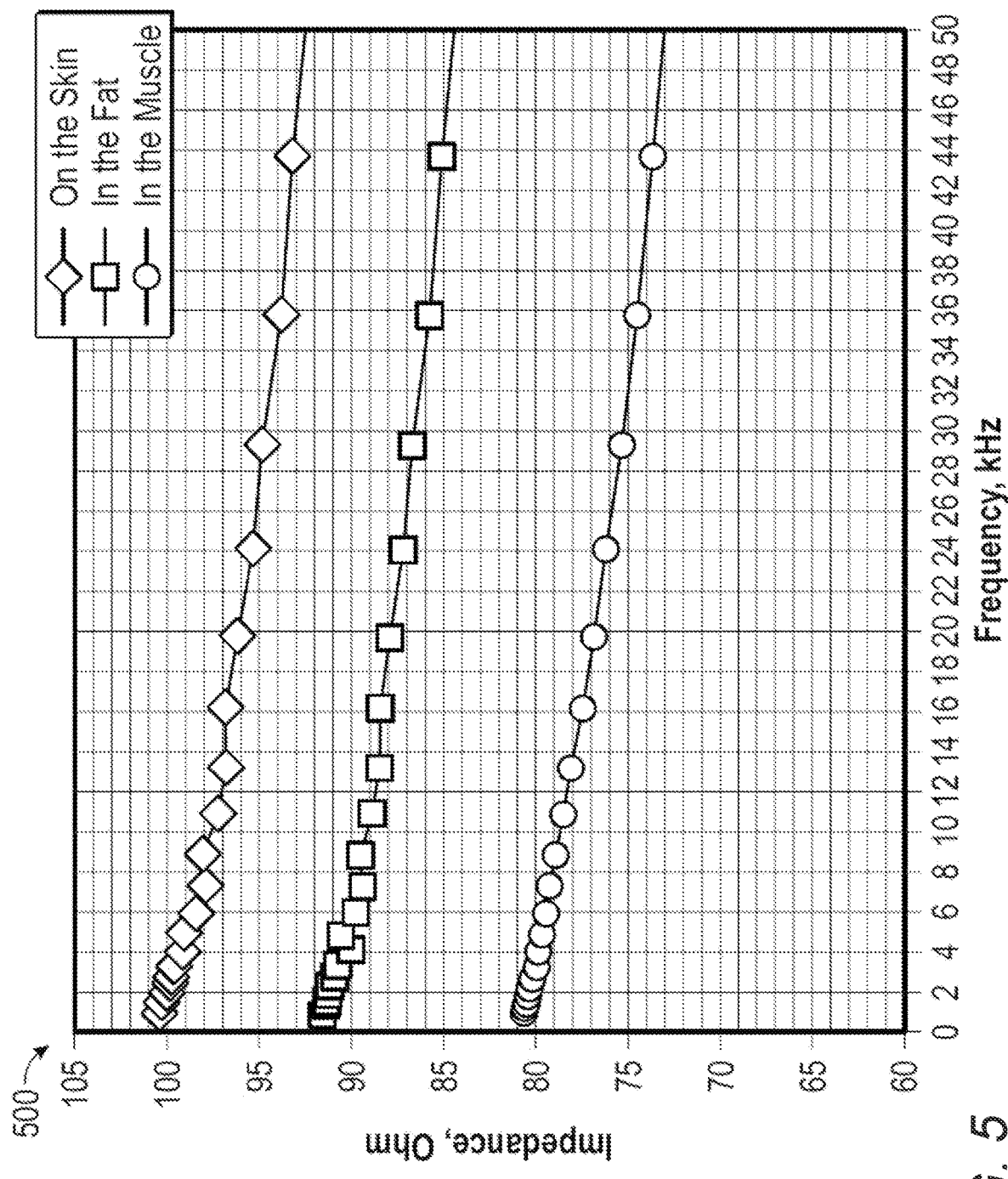
FIG. 5 is a graph showing bioimpedance measured at three different areas of tissue, in accordance with a representative embodiment.

FIG. 5 is a graph showing bioimpedance measured at three different areas of tissue, in accordance with a representative embodiment. Specifically, the graph 500 shows a study of skin impedance using a swine specimen, where it can be seen that skin resistance is higher in the skin when compared to fat and muscle for an applied current at a specific frequency. It will be understood, however, that this graph 500 merely provides an example of the difference between the impedance of different tissue types—i.e., because the lowest frequency in this example study is 1 kHz, the composition of the skin may not be usefully determined. However, a small slope change can be seen between frequencies at 6 and 10 kHz from the skin measurement plot.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. For example, regarding the methods provided above, absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. An apparatus for measuring skin sodium content using bioimpedance spectroscopy, the apparatus comprising:
   a current generator structurally configured to produce a current at a predetermined frequency to apply to skin of a subject;
   a controller operable to adjust the predetermined frequency;
   a sensor structurally configured to measure voltage across the skin of the subject produced by the current; and
   at least one processor configured to determine, using the measured voltage, skin sodium content using a regression model including a formula, $SSC = a * \rho_{SR} + b * age + c$, where $\rho_{SR}$ is calculated skin resistivity, and wherein a, b, and c are constant coefficients configured to correlate skin sodium content obtained by sodium-magnetic resonance imaging with skin resistivity obtained by bioimpedance spectroscopy.

2. The apparatus of claim 1, wherein the at least one processor is configured to compute bioimpedance based on the measured voltage and to determine skin sodium content using the computed bioimpedance.

3. The apparatus of claim 1, wherein one or more of the current generator and the sensor includes a plurality of electrodes.

4. The apparatus of claim 1, wherein the controller is operable to control the current generator to produce current at a plurality of different frequencies.

5. The apparatus of claim 4, wherein the at least one processor is configured to determine one or more of a conductivity and a dielectric constant for current applied at the plurality of different frequencies.

6. The apparatus of claim 5, wherein the at least one processor is configured to determine a slope for one or more of the conductivity and the dielectric constant between at least two of the plurality of different frequencies.

7. The apparatus of claim 6, wherein the at least one processor is configured to determine a tissue type using the slope.

8. The apparatus of claim 1, further comprising a computing device in communication with the at least one processor.

9. The apparatus of claim 8, wherein the at least one processor is configured to transmit data to the computing device, the data including one or more of the predetermined frequency, the voltage, the resistance, skin resistivity, and the skin sodium content.

10. The apparatus of claim 1, wherein the at least one processor is configured to calculate skin resistivity at the predetermined frequency, wherein the skin sodium content is determined at least in part using the calculated skin resistivity.

11. The apparatus of claim 10, wherein the skin resistivity ($\rho_{SR}$) is calculated using a formula, $\rho_{SR}=R_F*A/L$, where $R_F$ is the resistance at the predetermined frequency, A is a cross-sectional area of a measurement region of the skin, and L is a distance between electrodes that measured the voltage.

12. The apparatus of claim 1, wherein the predetermined frequency is in a range between 1 Hertz (Hz) and 1 megahertz (MHz).

13. The apparatus of claim 1, wherein the current produced by the current generator is configured for application to dermis of the subject, and wherein the predetermined frequency is selected to traverse through the dermis of the subject.

14. The apparatus of claim 1, wherein one or more of the at least one processor and the controller is configured to:
 alter the predetermined frequency;
 repeat measurement of the voltage and determining the resistance at the altered frequency to determine a tissue type of the subject; and
 select the altered frequency determined to provide skin resistivity for dermis of the subject.

15. The apparatus of claim 1, wherein the at least one processor is configured to:
 determine one or more of a conductivity and a dielectric constant for current applied at a plurality of different frequencies;
 determine a slope for one or more of the conductivity and the dielectric constant between at least two of the plurality of different frequencies; and
 determine a tissue type using the slope.

16. The apparatus of claim 15, wherein the tissue type includes one of skin, fat, and muscle, and wherein tissue types of fat and muscle are disregarded for calculating skin sodium content.

17. The apparatus of claim 15, wherein the tissue type includes one of epidermis, dermis, and subcutaneous layer, and wherein all tissue types except the dermis are disregarded for calculating skin sodium content.

18. The apparatus of claim 1, wherein the at least one processor is configured to associate the skin sodium content with a physiological characteristic to determine a predictive health condition of the subject.

19. The apparatus of claim 1, wherein the at least one processor is configured to determine extracellular volume (ECV) and intracellular volume (ICV) of the skin.

20. The apparatus of claim 1, wherein the at least one processor is configured to:
 continuously calculate skin sodium content for a predetermined time period; and
 transmit a notification when skin sodium content is outside of a predetermined range.

* * * * *